(12) United States Patent
Yun et al.

(10) Patent No.: US 8,637,700 B2
(45) Date of Patent: Jan. 28, 2014

(54) METHOD FOR PREPARING (3S,4S)-4-((R)-2-(BENZYLOXY)TRIDECYL)-3-HEXYL-2-OXETANONE AND NOVEL INTERMEDIATE USED THEREFOR

(75) Inventors: Sang Min Yun, Seongnam-si (KR); Dong Jin Hong, Incheon (KR); Weon Ki Yang, Hwaseong-si (KR); Jae Ho Yoo, Seoul (KR); Ji Sook Kim, Gyeonggi-do (KR); Moon Sub Lee, Bucheon-si (KR); Han Kyong Kim, Yongin-si (KR); Eun Jung Lim, Daegu (KR); Young Ho Moon, Suwon-si (KR); Young-Kil Chang, Seoul (KR); Gwan Sun Lee, Seoul (KR)

(73) Assignee: Hanmi Science Co., Ltd, Hwaseong-Si (KR)

( * ) Notice: Subject to any disclaimer, the term of this patent is extended or adjusted under 35 U.S.C. 154(b) by 485 days.

(21) Appl. No.: 13/120,561

(22) PCT Filed: Oct. 30, 2009

(86) PCT No.: PCT/KR2009/006338
§ 371 (c)(1),
(2), (4) Date: Mar. 23, 2011

(87) PCT Pub. No.: WO2010/053275
PCT Pub. Date: May 14, 2010

(65) Prior Publication Data
US 2011/0178330 A1   Jul. 21, 2011

(30) Foreign Application Priority Data

Nov. 4, 2008  (KR) .................. 10-2008-0108991

(51) Int. Cl.
*C07D 319/08* (2006.01)
*C07D 305/08* (2006.01)

(52) U.S. Cl.
USPC ............ 562/587; 562/579; 549/263; 549/328

(58) Field of Classification Search
None
See application file for complete search history.

(56) References Cited

U.S. PATENT DOCUMENTS

| 5,245,056 A | 9/1993 | Karpf et al. |
| 6,392,061 B1 | 5/2002 | Gentry Mullins |
| 2002/0045767 A1 | 4/2002 | Gentry Mullins |

FOREIGN PATENT DOCUMENTS

WO  2004/065346 A1  8/2004

OTHER PUBLICATIONS

Ma et al., "Total Synthesis and Comparative Analysis of Orlistat, Valilactone, and a Transposed Orlistat Derivative: Inhibitors of Fatty Acid Synthase," Organic Letters, 2006, vol. 8, No. 20, pp. 4497-4500.
Ghosh et al., "Asymmetric Synthesis of (−)-Tetrahydrolipstatin: An anti-Aldol-Based Strategy," Organic Letters, 2000, vol. 2, No. 16, pp. 2405-2407.
Dirat et al., "Oxazoline N-Oxide-Mediated [2+3] Cycloadditions. Application to a Synthesis of (+)-Tetrahydrolipstatin," Organic Letters, 1999, vol. 1, No. 5, pp. 753-755.
Taiwanese Patent Office, Taiwanese Office Action issued in corresponding TW Application No. 098137215, dated Jun. 21, 2012.
Barbier et al., "Synthesis of Tetrahydrolipstatin and Tetrahydroesterastin, Compounds with a Beta-Lactone Moiety. Stereoselective Hydrogenation of a Beta-Keto delta-Lactone and Conversion of the delta-Lactone into a Beta-Lactone," J. Org. Chem., 1988, vol. 53, No. 6, pp. 1218-1221.

*Primary Examiner* — Yevegeny Valenrod
(74) *Attorney, Agent, or Firm* — Sughrue Mion, PLLC

(57) ABSTRACT

The present invention relates to a high-yield method for preparing highly pure (3S,4S)-4-((R)-2-(benzyloxy)tridecyl)-3-hexyl-2-oxetanone using a metal salt of (2S,3S,5R)-2-hexyl-3,5-dihydroxyhexadecanoic acid as an intermediate.

11 Claims, No Drawings

METHOD FOR PREPARING (3S,4S)-4-((R)-2-(BENZYLOXY)TRIDECYL)-3-HEXYL-2-OXETANONE AND NOVEL INTERMEDIATE USED THEREFOR

FIELD OF THE INVENTION

The present invention relates to a method for preparing (3S,4S)-4-((R)-2-(benzyloxy)tridecyl)-3-hexyl-2-oxetanone and a novel intermediate used therefor.

BACKGROUND OF THE INVENTION (3S,4S)-4-((R)-2-(benzyloxy)tridecyl)-3-hexyl-2-oxetanone of formula I is known for its usefulness as an intermediate for the preparation of tetrahydrolipstatin (orlistat) (U.S. Pat. Nos. 5,245,056 and 5,399,720, and Mark A. Schwindt. et. Al., Org. Process Research, December 2007, 524).

(2S,3S,5R)-3-hexyl-4-hydroxy-6-undecyltetrahydropyran-2-one of formula IV has been used as the key starting material in the preparation of optically pure (3S,4S)-4-((R)-2-(benzyloxy)tridecyl)-3-hexyl-2-oxetanone of formula I or a derivative thereof having an easily deprotectable alkyl protecting group.

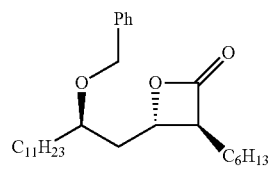
<Formula I>

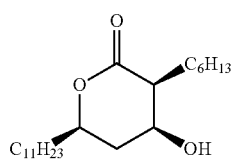
<Formula IV>

Such a preparative procedure, as described in U.S. Pat. No. 5,245,056, involves several steps as shown in scheme I:

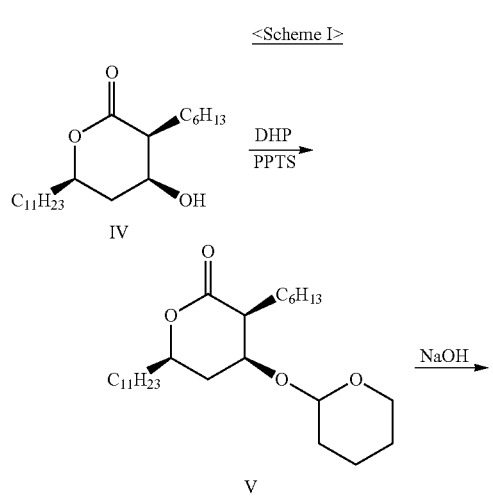
<Scheme I>

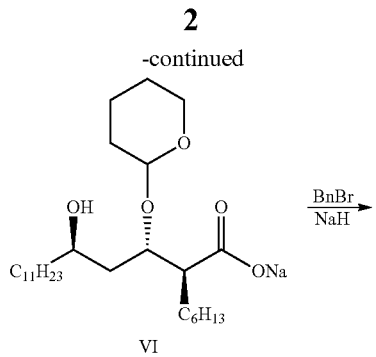

That is, the compound of formula V is prepared by introducing a tetrahydropyranyl group to protect the hydroxy group of the compound of formula IV. Then, the compound of formula V is hydrolyzed to obtain the compound of formula VI, which is treated with a benzylation reagent to obtain the compound of formula VII. A deprotection reaction is conducted by treating the compound of formula VII with an acid, followed by an optical resolution of the resulting compound, to obtain optically pure (2S,3S,5R)-5-benzyloxy-2-hexyl-3-hydroxyhexadecanoic acid of formula II. Finally, cyclization of the compound of formula II is conducted to obtain (3S,4S)-4-(R)-2-(benzyloxy)tridecyl)-3-hexyl-2-oxetanone of formula I.

However, the method has the problems of using complicated reaction steps that result in a low overall yield.

As for an alternative method, Korean Patent No. 191,365 discloses a procedure for preparing the compound of formula II starting from the compound of formula IV, as shown in scheme II:

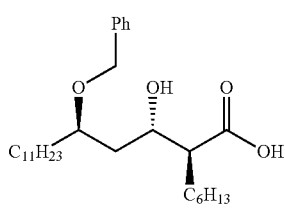

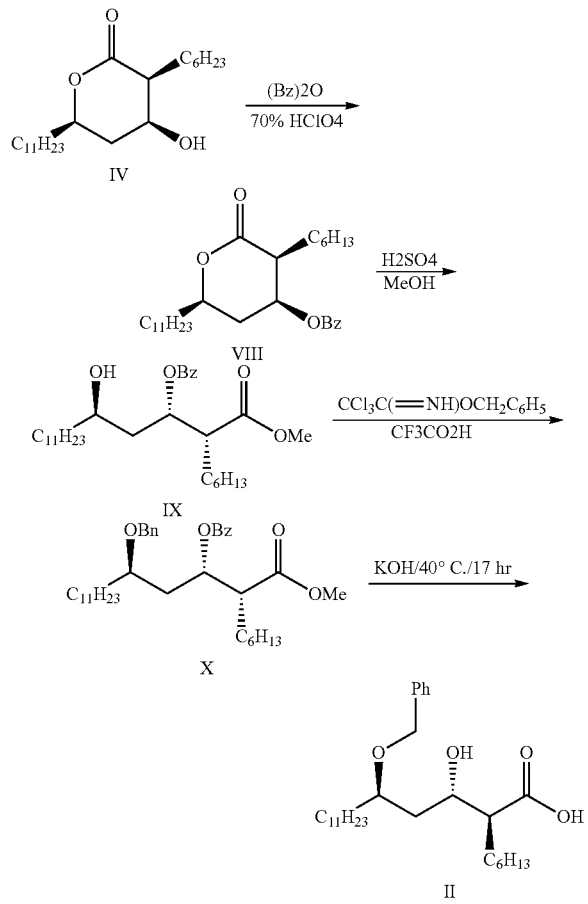

The above procedure comprises: protecting the hydroxy group of the compound of formula IV by introducing a benzoyl group thereto, to obtain the compound of formula VIII, hydrolyzing the compound of formula VIII to obtain a compound of formula IX which is subject to benzylation reaction to obtain the compound of formula X, and the compound of formula X is hydrolyzed to obtain the compound of formula II. The above method also gives a low yield.

However, this method have problems in that the protection and the substituent deprotection of the hydroxy group of formula IV should be conducted; a hindrance is occurred and strong reaction conditions for benzylation are required, due to the structure of the compound of formula VIII which comprises a sterically large benzoyl group adjacent to the hydroxy group of 5' position; and its overall yield is as low as 41.2%.

U.S. Pat. No. 5,399,720 discloses a method for preparing the benzylamine salt of (2S,3S,5R)-5-benzyloxy-2-hexyl-hydroxyhexadecanoic acid of formula IIa by way of using the compound of formula IV as a starting material, as shown in scheme III:

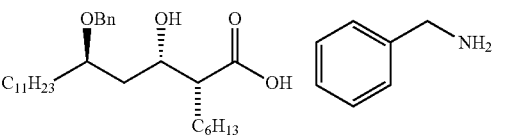

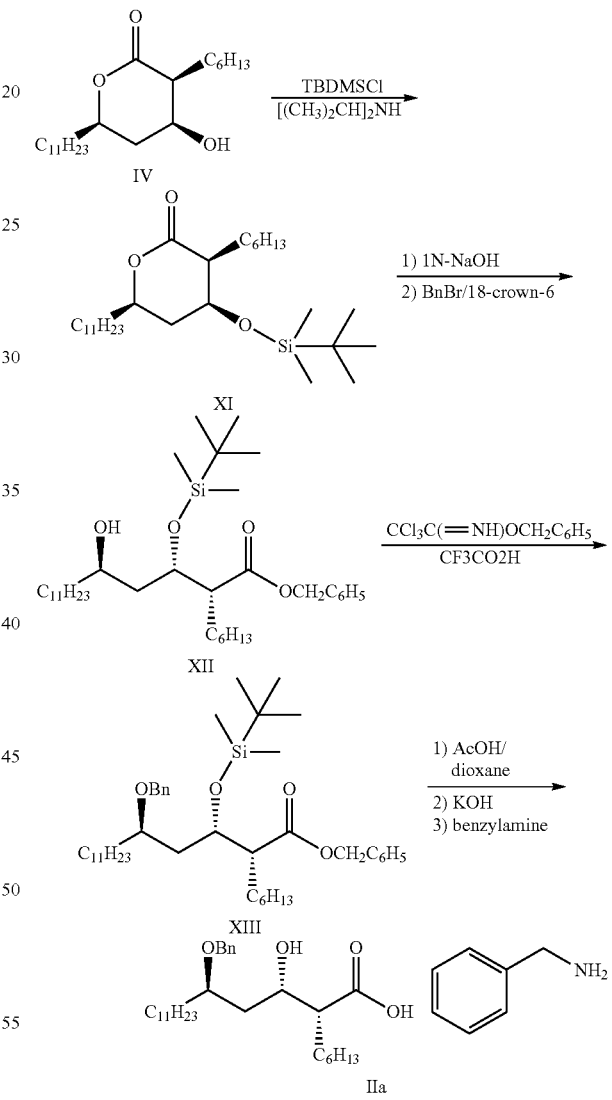

However, this method also suffers from the problems of a low overall yield (43%) due to the necessity of strong benzylation conditions and the necessity to conduct deprotection and hydrolyzation steps after the benzylation.

The present inventors have endeavored to solve the above problems of the methods of the prior art; and have found that the subject compound can be prepared in a high yield and high purity by hydrolyzing the compound of formula IV without protecting its hydroxyl group and subjecting the resulting compound to selective benzylation and cyclization.

SUMMARY OF THE INVENTION

Accordingly, it is an object of the present invention to provide an improved method for preparing (3S,4S)-4-((R)-2-(benzyloxy)tridecyl)-3-hexyl-2-oxetanone of formula I using a novel intermediate.

DETAILED DESCRIPTION OF THE INVENTION

The present invention provides a high-yield method for preparing highly pure (3S,4S)-4-((R)-2-(benzyloxy)tridecyl)-3-hexyl-2-oxetanone of formula I comprising 1) treating a compound of formula IV with a metal hydroxide in a solvent to prepare the compound of formula III;

2) treating the compound of formula III with a benzylation reagent in a solvent in the presence of a base to prepare the compound of formula II; and 3) subjecting the compound of formula II to a cyclization reaction to obtain the compound of formula I:

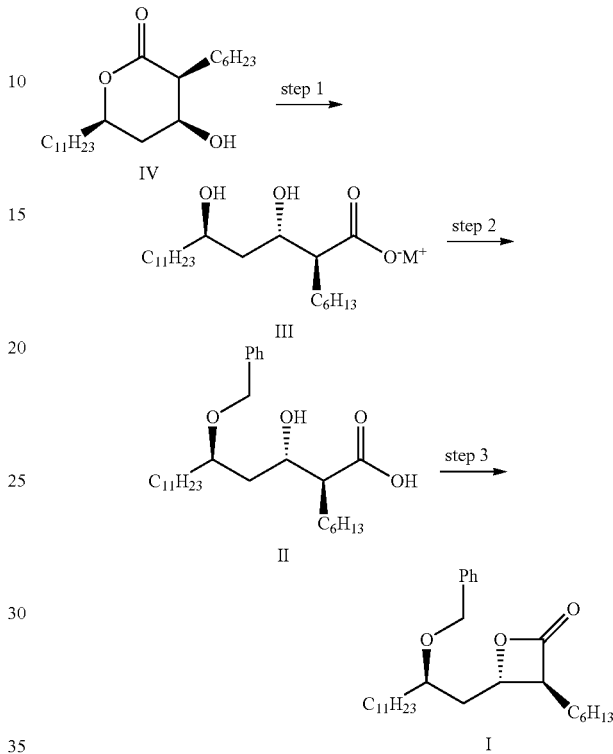

<Formula I>

<Formula II>

<Formula III>

<Formula IV> wherein,
M is Na, K, or Li.

In accordance with another aspect of the present invention, there is provided a metal salt of (2S,3S,5R)-2-hexyl-3,5-dihydroxyhexadecanoic acid which is useful as an intermediate for the above method.

(3S,4S)-4-((R)-2-(benzyloxy)tridecyl)-3-hexyl-2-oxetanone of formula I according to the present invention may be prepared by synthetic route as shown in Scheme IV:

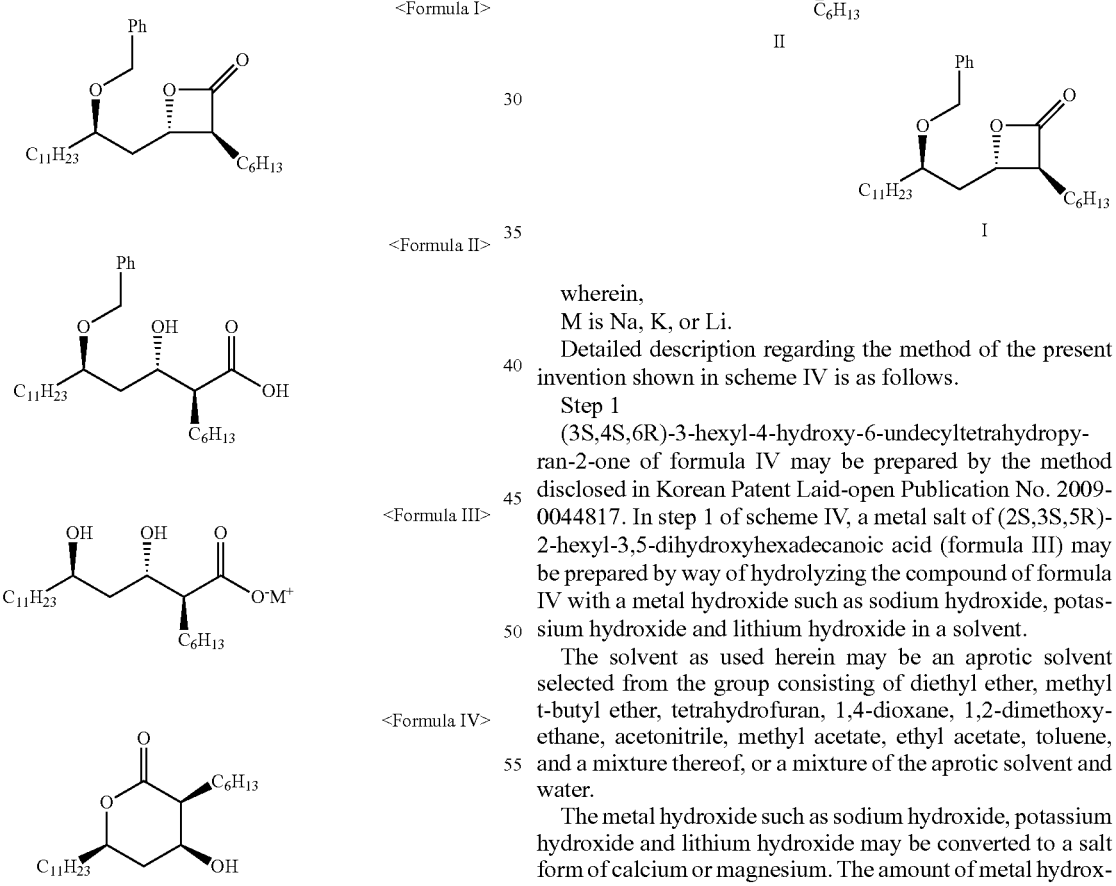

<Scheme IV> wherein,
M is Na, K, or Li.

Detailed description regarding the method of the present invention shown in scheme IV is as follows.

Step 1

(3S,4S,6R)-3-hexyl-4-hydroxy-6-undecyltetrahydropyran-2-one of formula IV may be prepared by the method disclosed in Korean Patent Laid-open Publication No. 2009-0044817. In step 1 of scheme IV, a metal salt of (2S,3S,5R)-2-hexyl-3,5-dihydroxyhexadecanoic acid (formula III) may be prepared by way of hydrolyzing the compound of formula IV with a metal hydroxide such as sodium hydroxide, potassium hydroxide and lithium hydroxide in a solvent.

The solvent as used herein may be an aprotic solvent selected from the group consisting of diethyl ether, methyl t-butyl ether, tetrahydrofuran, 1,4-dioxane, 1,2-dimethoxyethane, acetonitrile, methyl acetate, ethyl acetate, toluene, and a mixture thereof, or a mixture of the aprotic solvent and water.

The metal hydroxide such as sodium hydroxide, potassium hydroxide and lithium hydroxide may be converted to a salt form of calcium or magnesium. The amount of metal hydroxide to be used is in the range of 1 to 50 mole equivalents, preferably 1 to 3 mole equivalents, more preferably 1.05 to 1.2 mole equivalents, based on the compound of formula IV.

The reaction of step 1 may be conducted at a temperature ranging from 0° C. to boiling point of solvent, preferably 30° C. to 80° C.

The compound of formula III thus obtained can be used in step 2 without further purification, and is useful as an intermediate for preparing (3S,4S)-4-((R)-2-(benzyloxy)tridecyl)-3-hexyl-2-oxetanone of formula I.

Step 2

In step 2, the compound of formula III obtained in the above step 1 is subjected to a benzylation without introducing a protecting group thereto in a solvent in the presence of a base, to prepare (2S,3S,5R)-5-benzyloxy-2-hexyl-3-hydroxyhexadecanoic acid of formula II wherein a benzyl group is selectively introduced at 5' position.

The solvent as used herein may be an aprotic solvent selected from the group consisting of tetrahydrofuran, diethyl ether, methyl t-butyl ether, 1,2-dimethoxyethane, 1,4-dioxane, dichloromethane, dichloroethane, acetonitrile, methyl acetate, ethyl acetate, toluene, N,N-dimethylformimide, dimethyl sulfoxide and a mixture thereof, or a mixture of the aprotic solvent and water. The preferred solvent as used herein is tetrahydrofuran, methyl t-butyl ether or 1,2-dimethoxyethane.

In the meantime, the base as used herein may be lithium hydroxide, sodium hydroxide, potassium hydroxide, lithium t-butoxide, sodium t-butoxide or potassium t-butoxide, and the amount of the base to be used is in the range of 1 to 5 mole equivalents, preferably 1 to 3 mole equivalents, more preferably 1.05 to 2.0 mole equivalents, based on the compound of formula III.

Benzylation reagent as used herein for benzylation may be an optionally substituted benzyl halide such as benzyl chloride, benzyl bromide, and benzyl iodide, and considering reactivity, benzyl bromide is preferred. The amount of the benzylation reagent to be used is in the range of 1 to 5 mole equivalents, preferably 1 to 3 mole equivalents, more preferably 1.05 to 2.0 mole equivalents, based on the compound of formula III.

The reaction of step 2 may be conducted at a temperature ranging from 0° C. to boiling point of the solvent, preferably 10° C. to 100° C. Additives such as tetrabutylammonium iodide may be used to increase reaction rate.

Further, in order to easily obtain (2S,3S,5R)-5-benzyloxy-2-hexyl-3-hydroxyhexadecanoic acid of formula II in form of crystals in a purification process, an amine base may be added to the reaction to convert (2S,3S,5R)-5-benzyloxy-2-hexyl-3-hydroxyhexadecanoic acid to its amine salt.

Step 3

In step 3, (3S,4S)-4-((R)-2-(benzyloxy)tridecyl)-3-hexyl-2-oxetanone of formula I may be prepared by cyclization of (2S,3S,5R)-5-benzyloxy-2-hexyl-3-hydroxyhexadecanoic acid of formula II with a cyclization reagent. Said 3-hydroxyhexadecanoic acid having a protecting group at the 5' position may be converted to oxetanone by employing benzenesulfonyl chloride in pyridine, as described in U.S. Pat. Nos. 4,983,746 and 5,245,056.

(3S,4S)-4-((R)-2-(benzyloxy)tridecyl)-3-hexyl-2-oxetanone of formula I, prepared through the above 3 steps may be subjected to an additional debenzylation to produce (3S,4S)-3-hexyl-4-((R)-2-hydroxytridecyl)-2-oxetanone, which may be used for preparing orlistat.

The present invention will be described in further detail with reference to the following Examples. However, it should be understood that the present invention is not restricted by the specific Examples.

Example 1

Preparation of sodium (2S,3S,5R)-3,5-dihydroxy-2-hexyl-hexadecanoate (compound of formula III)-(1)

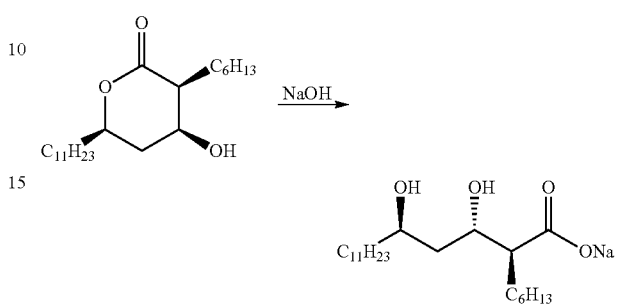

25.5 g of (2S,3S,5R)-3-hexyl-4-hydroxy-6-undecyltetrahydropyran-2-one was dissolved in 178.5 mL of methyl-t-butyl ether, 90 mL of 2N NaOH solution was added to thereto, and the resulting solution was stirred for 3 hours while keep the mixed solution's temperature at 50° C. The reaction mixture was then kept still until phase separation occurred, the aqueous layer thereof was removed, and the remaining organic phase was washed twice with 100 mL portions of salt water. The organic solution thus obtained was dried over anhydrous sodium sulfate, filtered, and distilled to remove the solvent under a reduced pressure, to obtain 28.4 g of the title compound (yield: 100%) as an oil.

$^1$H-NMR, 300 MHz (CD$_3$OD, ppm): δ 0.89 (dd, 6H, J=5.8, 1.2 Hz), 1.24-4.80 (m, 32H), 2.10 2.49 (m, 2H), 3.72-3.87 (m, 1H)

Example 2

Preparation of methylbenzylamine salt of (2S,3S, 5R)-5-benzyloxy-2-hexyl-3-hydroxyhexadecanoic acid (compound of formula II)-(1)

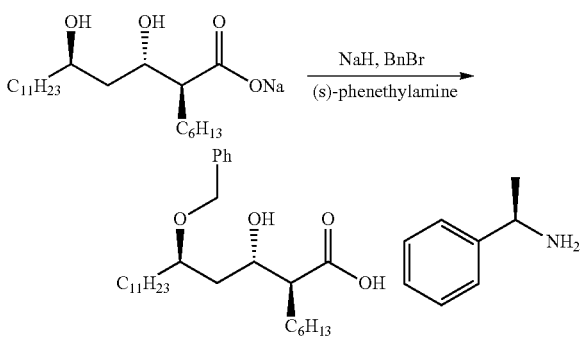

98 mL of sodium (2S,3S,5R)-3,5-dihydroxy-2-hexyl-hexadecanoate obtained from above Example 1 was dissolved in a mixed solvent of 98 mL of tetrahydrofuran and 328 mL of methyl-t-butyl ether. The reaction mixture was cooled to 0° C. and 7.19 g of sodium hydride and 30.7 g of benzylbromide were sequentially added to the mixed solution. Then the reaction mixture's temperature was raised to 60° C. and the reaction mixture was refluxed for 5 days (step (a)). After cooling the reaction mixture to room temperature, its pH was adjusted to 1, and the solution was stirred at room temperature for 3 hours. Then, pH of the reaction mixture was adjusted to 4, and the mixed solution was kept still until phase separation occurred. The aqueous layer thereof was removed and remaining organic phase was washed twice with 120 mL portions of salt water. The organic solution obtained above was dried over anhydrous magnesium sulfate, filtered, and distilled to remove the solvent under a reduced pressure. 438 mL of methyl acetate was added thereto and 8.7 g of (S)-α-methylbenzylamine slowly while stirring the mixture. After stirring for 3 hours, the mixture was cooled to 5° C., and further stirred 1 hour (step (b)). The mixture was dried and filtered, to obtain 31.1 g of the title compound (yield: 74%) as a white solid.

m.p. 104-106° C.

$^1$H-NMR (300 MHz, CDCl$_3$): 0.85-0.91 (m, 6H), 1.24 (m, 26H), 1.54 (d, 3H), 1.71-1.39 (m, 6H), 2.09-2.16 (m, 1H), 3.70-3.72 (m, 1H), 3.85-3.90 (m, 1H), 4.18 (q, 1H), 4.52 (d, 2H), 6.10 (bs, 5.0), 7.36-7.22 (m, 10H)

Example 3

Preparation of sodium (2S,3S,5R)-3,5-dihydroxy-2-hexyl-hexadecanoate (compound of formula III)-(2)

300 g of (2S,3S,5R)-3-hexyl-4-hydroxy-6-undecyltetrahydropyran-2-one was dissolved in 1.8 L of methyl-t-butyl ether. 9 L of 2N NaOH solution was added to the reaction mixture and the temperature of the reaction mixture was raised slowly and the aqueous layer thereof was separated and removed from the reaction mixture. The organic layer thereof was separated from the remaining the reaction mixture and washed by 450 mL portions of saturated salt water, and the solvent was removed under reduced pressure. 900 mL of toluene was added to the residue and the solvent and moisture were removed by azeotropic distillation under reduced pressure. 1.8 L of heptanes and 1.8 L of methyl-t-butyl ether was added to the residue, and the temperature of the reaction mixture was raised to 40° C. Then, the reaction mixture was cooled at room temperature and 50 mL of methanol was added thereto. When starting the formation of crystal, the reaction mixture was stirred at room temperature for 2 hours. The reaction mixture was then cooled to 10° C. and stirred for 30 minutes. Then the reaction mixture was filtered and dried with warm wind, to obtain 534 g of the title compound (yield: 96%).

Differential scanning calorimetry (DSC): 109.29-117.30° C.

$^1$H-NMR, 300 MHz (CD$_3$OD, ppm): δ 0.89 (dd, 6H, J=5.8, 1.2 Hz), 1.24-1.80 (m, 32H), 2.10 2.49 (m, 2H), 3.72-3.87 (m, 1H)

Example 4

Preparation of methylbenzylamine salt of (2S,3S, 5R)-5-benzyloxy-2-hexyl-3-hydroxyhexadecanoic acid (compound of formula II)-(2)

300 g of sodium (2S,3S,5R)-3,5-dihydroxy-2-hexyl-hexadecanoate obtained from above Example 3 was dissolved in a mixed solvent of 405 mL of toluene and 45 mL of dimethyl sulfoxide. The reaction mixture was cooled to 5° C. and 49.8 g (1.5 equivalents) of 55% sodium hydride and stirred at the same temperature for 30 minutes. Then, 325 g of benzylbromide was added thereto. The temperature of the reacting mixture was adjusted to 15° C. and the reaction mixture was stirred for 18 hours. Then, the same reaction as described step (b) of Example 2 was accomplished, and the solid obtained by said reaction was filtered and dried, to obtain 332.9 g of the title compound (yield: 75%) as a white solid.

The same analysis results as those of Example 2 were obtained.

Example 5

Preparation of methylbenzylamine salt of (2S,3S, 5R)-5-benzyloxy-2-hexyl-3-hydroxyhexadecanoic acid (compound of formula II)-(3)

100 g of sodium (2S,3S,5R)-3,5-dihydroxy-2-hexyl-hexadecanoate obtained from above Example 3 was dissolved in 1.5 L of toluene. 108.4 g of benzylbromide and 48.3 g of potassium-t-butoxide were sequentially added to the reaction mixture. Then the temperature thereof was slowly raised to 60° C. to 75° C. and the reaction mixture was heated for 12 hours. Then, the same reaction as described step (b) of Example 2 was accomplished, and the solid obtained by said reaction was filtered and dried, to obtain 106 g of the title compound (yield: 72%) as a white solid.

The same analysis results as those of Example 2 were obtained.

Example 6

Preparation of (3S,4S)-4-(R)-2(benzyloxy)tridecyl)-3-hexyl-2-oxetanone (compound of formula I)

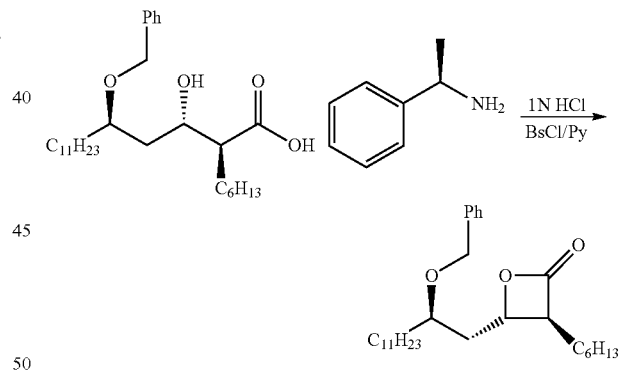

330 g of methylbenzylamine salt of (2S,3S,5R)-5-benzyloxy-2-hexyl-3-hydroxyhexadecanoic acid obtained from above Example 4 was dissolved in a mixed solvent of 1.65 L of hexane and 1.65 L of 2N hydrochloride aqueous solution. After stirring for 2 hours, the aqueous layer thereof was removed and remaining organic phase thereof was washed twice with 1.65 L portions of distilled water. The organic solution obtained above was dried over anhydrous magnesium sulfate, filtered, and distilled under a reduced pressure. Then, 2.61 L of pyridine was added thereto, and the reaction mixture was cooled to 0° C. and stirred. Further, 1.44 L of benzenesulfonyl chloride was slowly added thereto over 2 hours, and the reaction mixture was stirred for further 20 hours at the same temperature. After addition of 2.61 L of distilled water and 2.61 L of hexane, the reaction mixture was stirred strongly. Then, the reaction mixture was kept still until phase separation occurred and the aqueous layer thereof was removed from the reaction mixture. The organic solution obtained above was washed twice with 2.61 L portions of 2N hydrochloride and further washed twice 2.61 L portions of distilled water. The organic solution obtained above was dried over anhydrous magnesium sulfate and filtered, and then the solvent was removed under a reduced pressure. Accordingly, the 270.1 g of the title compound (yield: 101.2%) as a white solid was obtained.

$^1$H-NMR (300 MHz, CDCl$_3$): 0.80 0.95 (m, 6H), 1.15-1.85 (m, 30H), 1.94 (t, 2H, J=Hz), 3.15-3.26 (m, 1H), 3.55-3.65 (m, 1H), 4.35-4.63 (m, 3H), 7.25-7.40 (m, 5H)

Reference Example 1

Preparation of (3S,4S)-3-hexyl-4-((R)-2-hydroxy tridecyl)-2-oxetanone

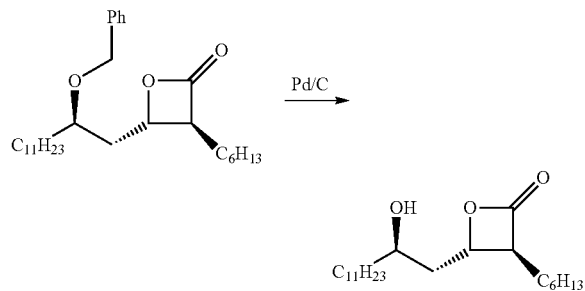

270 g of (3S,4S)-4-((R)-2(benzyloxy)tridecyl)-3-hexyl-2-oxetanone obtained from above Example 6 was dissolved in 1.89 L of ethyl acetate. 19 g of 5% Pd/c (Paladium/carbon) was added thereto, and the reaction mixture was stirred for 3 hours while raising the hydrogen pressure to 6 barn Pd was removed therefrom by filtration with Celite® and the solvent was removed under reduced pressure. 2.15 L of hexane was added thereto and the temperature of the reaction mixture was raised to 40° C. to melt the solid obtained above. Then, the reaction mixture was cooled to room temperature and crystal was formed in the reaction mixture at 20° C. After stirring for 8 hours, the reaction mixture was cooled to 5° C., stirred for 2 hours and filtered, to obtain 166.3 g of the title compound (yield: 83%) as a white solid.

m.p. 60-61° C.

$^1$H-NMR (300 MHz, CDCl$_3$): 4.54-4.44 (m, 1H), 3.87-3.74 (m, 1H), 3.3-3.16 (m, 1H), 1.95-1.12 (m, 32H), 0.88 (t-like, 6H)

Reference Example 2

Synthesis of Orlistat

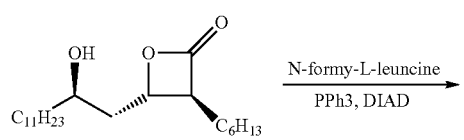

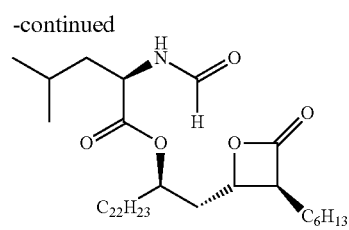

166 g of (3S,4S)-3-hexyl-4-((R)-2-hydroxy tridecyl)-2-oxetanone obtained from Reference Example 1 was dissolved in 830 mL of tetrahydrofuran. After the addition of 160 g of triphenylphosphine (PPh$_3$) and 86 g of N-formyl-L-leucine, the reaction mixture was cooled to 0° C. A mixed solution where 120 mL of diisopropylazodicarboxylate (DIAD) was diluted in 332 mL of tetrahydrofuran, was continuously added thereto over 1.5 hours. After stirring for further 30 minutes, the reaction mixture was stirred for 4 hours while slowly raising its temperature. After removing the solvent, 832 mL of hexane was added thereto, and the reaction mixture was stirred for 5 hours. The formed solid was removed therefrom by filtration, and the hexane layer thereof was washed with 499 mL of 55% methanol/distilled water three times. The remaining organic layer was dried over anhydrous magnesium sulfate and filtered, and then the solvent was removed under a reduced pressure. Then, 2.5 L of hexane was added thereto, and the reaction mixture was cooled to 10° C. and stirred for 1 hour, followed by addition of a seed of orlistat solid. The reaction mixture was slowly cooled to 0° C. again, and stirred overnight. The obtained solid was filtered, washed with 500 mL of cold hexane, and dried, to obtain 192.5 g of the title compound (yield: 83%) as a white solid.

m.p. 42.4-44.5° C.

$^1$H-NMR (300 MHz, CDCl$_3$): 8.22(s, 1H), 5.99 (d, 1H), 5.06-4.98 (m, 1H), 4.77-4.60 (m, 1H), 4.32-4.22 (m, 1H), 3.27-3.16 (m, 1H), 2.28-1.98 (m, 2H), 1.90-1.15 (m, 30H), 1.03-0.82 (m, 12H)

While the invention has been described with respect to the above specific embodiments, it should be recognized that various modifications and changes may be made to the invention by those skilled in the art which also fall within the scope of the invention as defined by the appended claims.

What is claimed is:

1. A method for preparing (3S,4S)-4-((R)-2-(benzyloxy)tridecyl)-3-hexyl-2-oxetanone of formula I comprising
   1) treating the compound of formula IV with a metal hydroxide in a solvent to prepare a compound of formula III;
   2) treating the compound of formula III with a bezylation reagent in a solvent in the presence of a base to prepare the compound of formula II; and
   3) subjecting the compound of formula II to a cyclization reaction to obtain the compound of formula I:

<Formula I>

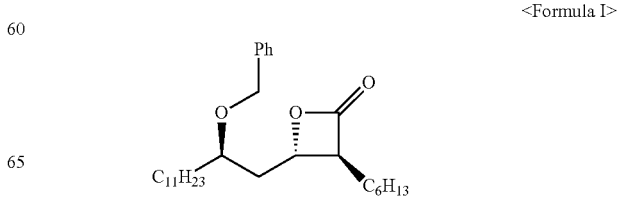

-continued

<Formula II>

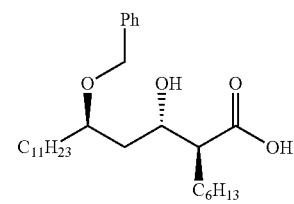

<Formula III>

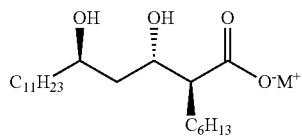

<Formula IV>

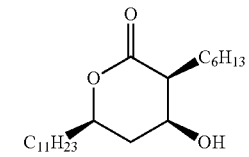

wherein,
M is Na, K, or Li.

2. The method of claim 1, wherein the solvent used in step 1) is an aprotic solvent selected from the group consisting of diethyl ether, methyl t-butyl ether, tetrahydrofuran, 1,4-dioxane, 1,2-dimethoxyethane, acetonitrile, methyl acetate, ethyl acetate, toluene and a mixture thereof, or a mixture of the aprotic solvent and water.

3. The method of claim 1, wherein the metal hydroxide in step 1) is used in an amount of 1 to 50 mole equivalents based on the compound of formula IV.

4. The method of claim 1, wherein the solvent used in step 2) is an aprotic solvent selected from the group consisting of tetrahydrofuran, diethyl ether, methyl t-butyl ether, 1,2-dimethoxyethane, 1,4-dioxane, dichloromethane, dichloroethane, acetonitrile, methyl acetate, ethyl acetate, toluene, N,N-dimethylformimide, dimethyl sulfoxide and a mixture thereof, or a mixture of the aprotic solvent and water.

5. The method of claim 1, wherein the base used in step 2) is selected from the group consisting of lithium hydroxide, sodium hydroxide, potassium hydroxide, lithium t-butoxide, sodium t-butoxide, and potassium t-butoxide.

6. The method of claim 5, wherein the base is used in an amount of 1 to 5 mole equivalents based on the compound of formula III.

7. The method of claim 1, wherein the benzylation reagent used in step 2) is benzyl halide selected from the group consisting of benzyl chloride, benzyl bromide, and benzyl iodide.

8. The method of claim 1, wherein the benzylation reagent in step 2) is used in an amount of 1 to 5 mole equivalents based on the compound of formula III.

9. A compound of formula III:

<Formula III>

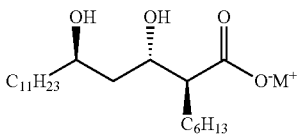

wherein,
M is Na, K, or Li.

10. A method for preparing the compound of formula III comprising the step of treating (3S,4S,6R)-3-hexyl-4-hydroxy-6-undecyltetrahydropyran-2-one of formula IV with a metal hydroxide in a solvent:

<Formula III>

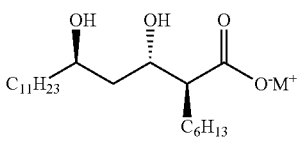

<Formula IV>

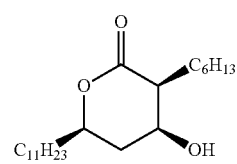

wherein,
M is Na, K, or Li.

11. A method for preparing the compound of formula II comprising the step of treating a metal salt of (2S,3S,5R)-3,5-dihydroxy-2-hexyl-hexadecanoic acid of formula III with a bezylation reagent in a solvent in the presence of a base:

<Formula II>

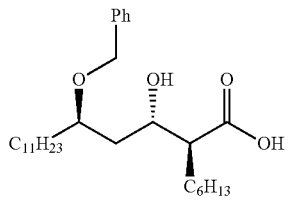

<Formula III>

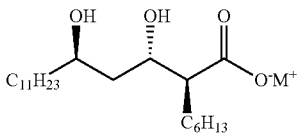

wherein,
M is Na, K, or Li.

* * * * *